United States Patent

Andry, III

[11] 4,123,125
[45] Oct. 31, 1978

[54] COMBINED DISPENSING AND INVENTORY CONTROL SYSTEM

[76] Inventor: Paul L. Andry, III, 2806 Soniat St., New Orleans, La. 70115

[21] Appl. No.: 736,455

[22] Filed: Oct. 28, 1976

[51] Int. Cl.² .......................... A47F 1/00; B65D 73/00
[52] U.S. Cl. ......................................... 312/35; 312/42; 312/234.1; 206/459
[58] Field of Search ............... 206/459, 63.3; 312/209, 312/235 T, 35 T, 350

[56] References Cited

U.S. PATENT DOCUMENTS

| | | | |
|---|---|---|---|
| 1,144,928 | 9/1915 | Adair et al. | 312/42 |
| 1,156,140 | 10/1915 | Hair | 312/42 |
| 3,266,860 | 8/1966 | Moore et al. | 312/350 |
| 3,337,172 | 8/1967 | Jackson | 312/245 |
| 3,347,358 | 10/1967 | Meyers | 206/459 |
| 3,407,781 | 10/1968 | Ardire | 206/459 |
| 3,528,715 | 9/1970 | Williams | 312/245 |
| 3,759,597 | 9/1973 | Johnson | 206/459 |
| 3,858,717 | 1/1975 | Peters | 206/459 |
| 3,987,897 | 10/1976 | Smith | 206/459 |

FOREIGN PATENT DOCUMENTS 817,449  7/1959  United Kingdom .................. 312/234.1

Primary Examiner—Mervin Stein
Assistant Examiner—Victor N. Sakran
Attorney, Agent, or Firm—C. Emmett Pugh & Associates

[57] ABSTRACT

A portable dispensing system for storing and dispensing, for example, surgical suture packages, which system provides one or more shelved dispenser boxes having a transparent front panel for allowing visual inspection of individual packages (and descriptive information on the packages) of sutures stored therein. The shelves of each dispenser box are adjustable as needed to retain different types of sutures thereon, with several shelves mountable in each dispenser box, thereby forming separate storage sectors.

Slots in the transparent front panel are provided for the addition and removal of individual suture packages to each shelved sector.

Inventory information is written on the transparent panel after visual inspection from which the status of suture packages therein is perceived.

Each suture dispenser box is slideably storable on a wall rack. Several racks can be mounted in various parts of a hospital and individual dispenser boxes shuttled to areas where need is greatest.

3 Claims, 6 Drawing Figures

U.S. Patent  Oct. 31, 1978  4,123,125
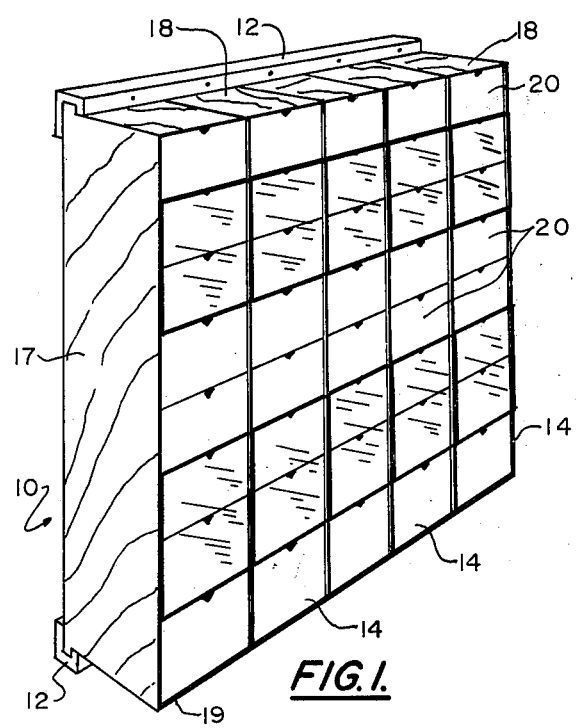
FIG.1.
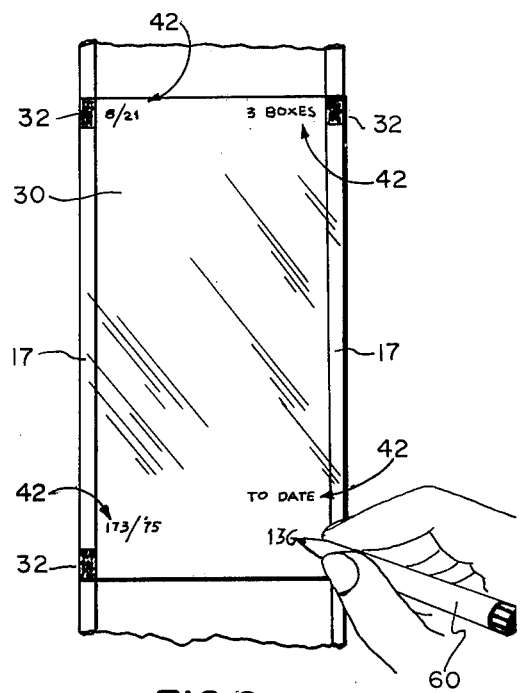
FIG.2.
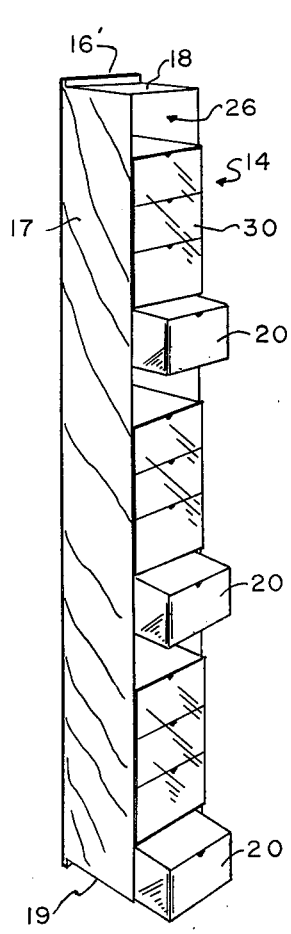
FIG.3.
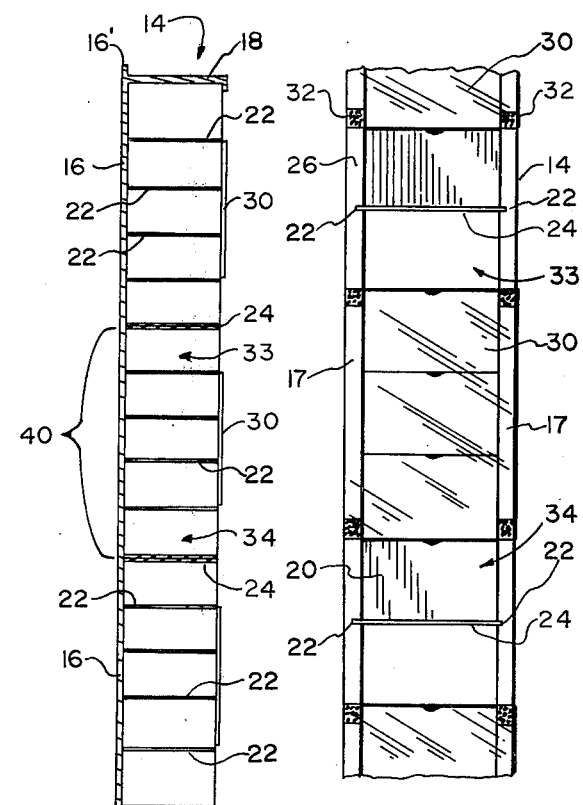
FIG.4.
FIG.5.
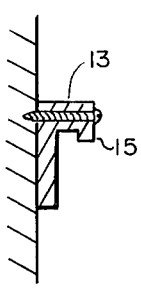
FIG.6.

COMBINED DISPENSING AND INVENTORY CONTROL SYSTEM

BACKGROUND OF THE INVENTION

1. Field of the Invention

The present invention relates to the storing and inventory control of surgical supplies. More particularly, the present invention relates to the storage of surgical sutures, and a system for the storage of suture packages in shelved racks which are fully adjustable for the maintenance of tight inventory control.

2. General Background

Over the past years, the numbers of different type of sutures has increased tremendously. Factors contributing to this increase are new materials, better manufacturing techniques, and more specialization. The greatest contributing factor, however, was the introduction of the "atramatic" suture or a suture with a needle attached. For each type of suture there is now a full range of sizes (diameters and strengths), lengths and needles. These needles are divided in several general types and for each type there are different sizes.

In many large hospitals, well over several hundred types of lengths and sizes of suture are stored in numbers of several boxes per type. This represents in many cases the single greatest expense that a surgery department has, and, naturally is the area needing greatest inventory control.

There are, however, several problems with the control of sutures. The first is that sutures are bulky and expensive, making buying in quantities inpractical. Thus it is very important to maintain enough sutures so that the supply is not depleted, but not so much that in an inordinate amount of space for storage is needed.

The second problem is that suture storage is messy. That is, boxes which contain the sutures do not stack well, and removing one box often results in two or three other types falling over and getting mixed up. A further problem is that sutures must be rotated. Each time a shipment arrives, the remaining sutures must be removed from the shelves, the new shipment placed in the back, and the existing stock placed in the front. This process is further complicated by the aforementioned problem of different types of sutures getting mixed. Rotation of sutures, although important, is often overlooked.

The fourth problem is that sutures are usually stored on open shelves or carts and collect dust. This is an extremely bad technique with any sterile supply in a "clean area". Also sutures must therefore be removed from the shelves for periodic cleaning and then restocked.

Another problem is that a suture must be maintained in a logical order (just as books in a library) for ease of location and inventory. As is usually the case, suture is arranged in some order initially, and no space is provided for additions. Consequently, when a new size or type arrives, it is often placed in some "convenient place" which has nothing to do with any original established order.

The aforementioned problems are compounded over the years, and with an inadequate storage system, hours can be wasted locating a particular suture package in the existing stock. A further problem is that the volume of a certain type of suture used changes constantly. As new products are introduced, old ones are no longer used. Doctors and procedures change resulting in the obsolescence of some sutures. There are usually no provisions for locating or returning to the manufacturer (for full credit) unused suture supplies. Overstocking and dead inventory tie up money as well as space. A further pitfall of dead inventory consists of those supplies which are received in error. Many times, these mistakes are not corrected immediately. The more time that lapses, the more likely that the suture will not be returned, resulting in financial losses. As previously mentioned, sutures must be restocked to prevent a shortage. Yet adjustments must be made as usage volume changes. This is complicated by the fact that distributors usually maintain poor inventories themselves and backorders become the rule rather than the exception. It is not uncommon in the hospital industry to have 20 separate shipments on the same order. To maintain an adequate inventory of sutures, the stock must be counted no less than once a week. Records must be kept of quantities orders, quantities maintained, quantities used, dates ordered, dates received and numbers received.

In summary, sutures are an expensive, widely diverse surgical supply. Its very nature requires close control for both economic and medical reasons. Neglect in its control results in loss of time, loss of money and loss of proper medical sterility standards.

3. Prior Patents

Several types of storage systems have been patented which provide dispensing containers for use with various products. A summary of these prior patents is listed in the following table:

| PRIOR PATENTS | | |
|---|---|---|
| Patent No. | Inventors | Issue Date |
| 1,156,140 | B. M. Hair | 10/12/15 |
| 1,464,343 | S. M. Scherer | 8/7/23 |
| 1,734,031 | W. C. Carlson | 11/5/29 |
| 1,980,819 | F. R. Nelson | 11/13/34 |
| 3,744,866 | Robert L. Cook | 7/10/73 |

4. General Discussion of the Present Invention

The present invention eliminates all the prior art problems and shortcomings in a simple and inexpensive manner. The present invention permits the storage and inventory control of large numbers and diverse types of suture packages. The suture dispensing system of the present invention provides a series of portable adjustable dispenser boxes. Each box is capable of holding a plurality of individual suture packages. Inside dimensions of each dispenser box is designed to accommodate stacks of individual boxes of sutures. Each dispenser box is provided with adjustable shelves slideably mountable in several slotted supports. The dispenser box is preferably rectangular and elongated, and vertically oriented. Front transparent panels have slots for the entry and removal of individual suture packages. The distance between entry and removal slots can be varied as necessary to accomodate different quantities of one type of suture. The adjustable shelves can be mounted to correspond to the entry and exit openings in the transparent front end. It is possible to maintain inventory records on the front transparent panels in an orderly manner. Individual dispenser boxes can be slideably mounted on a wall rack, allowing boxes to be removed and relocated as necessary.

BRIEF DESCRIPTION OF THE DRAWINGS

FIG. 1 is a prespective view of the preferred embodiment of the apparatus of the present invention;

FIG. 2 is a partial frontal view of the dispensing box of the preferred embodiment of the present invention illustrating the transparent inventory control panel;

FIG. 3 is a perspective view of an individual dispensing box of the preferred embodiment of the apparatus of the present invention;

FIG. 4 is a side sectional elevation view of a single dispensing box of the preferred embodiment of the apparatus of the present invention;

FIG. 5 is a partial frontal view of an individual dispensing box of the preferred embodiment of the apparatus of the present invention; and FIG. 6 is a sectional view of one of the wall mounting brackets of the holding rack of the apparatus of the present invention.

DETAILED DESCRIPTION OF THE PREFERRED EMBODIMENTS

As can best be seen in FIG. 1, the preferred embodiment of the suture dispensing system of the present invention, designated generally by the numeral 10, is comprised of a dispenser box holding rack 12 upon which a plurality of dispenser boxes 14 can be slideably mounted and stored. FIGS. 3 and 4 illustrate a single dispensing box 14 of the preferred embodiment of the apparatus of the present invention. Dispenser boxes 14 are generally elongated and preferably vertically stored. Each dispenser box 14 is comprised of a back wall 16, sidewalls 17, top 18 and bottom 19. Each dispenser box 14 can be sized to accomodate a plurality of identically sized packages 20 of, for example, surgical sutures.

Dispenser boxes 14 are provided with a plurality of slots 22 arranged in parallel, horizontal pairs and equally spaced from the top 18 of dispenser box to its bottom 19. Slots 22 are arranged in pairs (see FIG. 5) and are dimensioned to slideably receive adjustable shelves 24. Parallel slots 22 can be spaced a distance which would allow the insertion of a package 20 of suture on a shelf 24 if two shelves 24 were placed in two adjacent pairs of slots 22. Thus, it can be seen that virtually any combination of spacing arrangement could be achieved to accommodate any number of packages on a given shelf (i.e. one, two, or more packages 20 of suture as desired). As will be more fully explained hereinafter, this gives suture dispenser box 14 the capability of containing specific types of sutures in separated segments between shelves 24 as needed.

The construction of the dispenser boxes 14, as described above, leaves an open front portion 26 (see FIG. 3), allowing insertion of suture packages 20 into dispenser box 14. This open portion 26 is closed in part by the attachment of transparent writing panels 30 to the outer face 26 of side walls 17. The attachment of writing panels 30 to side walls 17 can be made by any conventional means. Examples of attachment means are: screws, nails, adhesive tape, glue, or Velcro. In the preferred embodiment, "Velcro" fasteners are used to provide a semi-permanent and adjustable fastening means. FIG. 2 illustrates the use of fasteners 32 to afix writing plates 30 to the faces 26 of side wall 17. It is desirable to have "Velcro" fasteners 32 placed linearly along the faces 26 of sidewall 17 in an orderly repetitively fashion which allows adjustable placement of writing panels 30 along the outer face 26 of side wall 17 as required to correspond with changes in the placement of shelves 24. If desired, writing panels 33 can be placed between the shelves 24 leaving an opening inlet 33 and a package removal outlet 34 so that suture packages 20 can be inserted into a given inlet 33 forming a stack and older suture packages 20 in the stack can be removed through outlet 34 when needed for use (see FIG. 5).

Thus, individual sectors 40 (see FIG. 4) could be formed in the apparatus of the present invention to house a specific type of suture in a compartment with other boxes of its same type. Each sector 40 would provide an opening 34 for the removal of older dated suture packages 20, and an inlet 33 for the addition of newer dated suture packages 20 as they were received by the hospital or like institution. Each sector 40 would allow the stacking of individual packages 20 from the bottom shelf 24 to an upper shelf 24 which could be adjustable as needed for the quantity of boxes 20 which would be desired to be stored together for a given suture type. The individual sector 40 would assure that older suture would have first use as the older suture would be removed from outlet 34, and newer suture as delivered to the institution from the manufacturer could be added to inlet 33 atop the existing stack of suture of a given type. It can be seen that an individual sector 40 in dispenser box 14 could be adjustable by the simple adjustment of shelves 24 into different slots of dispenser box 14. Writing panel 30 should be dimensioned differently for use with each sector 40, allowing for an inlet 33 and outlet 34 sized according to the cross sectional dimensions of a suture package 20, thereby allowing for easy entry or exit from outlet or inlet openings, 33, 34 respectively.

Writing panels 30 are preferably transparent, and can be made of any transparent material, for example, glass, plexi-glass and the like. In the preferred embodiment, a plexi-glass panel is utilized because of its relatively resilient nature. Writing panel 30 can be inscribed with inventory information suited to the individual hospital or institution needs. It should be understood that when the terms "writing" or "written" are used in the present application, reference is being made to any type of symbolic representation sufficient to convey inventory and stock storage information to the user. The information can be written by an individual using a hand-held device (e.g., pencil or the like) or it can be attached by using separate printed digits, rotating digit counters, or like devices. Writing panel 30 can be inscribed using a variety of conventional writing instruments (for example, grease pencils, Marks-a-Lot, felt tip pens and the like). In the preferred embodiment of the present invention, inventory information is transcribed at the corner sections 42 of transparent writing panels 30 using grease pencil 60.

An example (illustrated by FIG. 2) of a method for maintaining inventory records on writing panel 30 is hereinafter described. Initial quantities are established (in multiples of threes, for example) by volume usage. Visual inspection tells how many boxes of sutures 20 are needed to maintain a desired fixed supply. The date of an order (entered as "8-21" in FIG. 2) to the desired suture manufacturer is written using grease pencil 60 or the like on the left side of the writing panel 30. The quantity of packages 20 ordered is inscribed on the right portion of the plexi-glass panel 30. In the illustrative example of FIG. 2, three boxes were ordered on August 21. A total quantity of suture packages 20 used "to date" is written on a space on the bottom right hand portion of writing panel 30, (a total of "136" is illustrated in FIG. 2), and a total quantity of packages 20 ordered for the previous year is written in a space on the bottom left hand portion of writing panel 30. In FIG. 2, and exemplary "173" packages have been ordered for the year "1975" as shown by the symbols "173/75" at corner 42 of panel 30. When an order is received from the manufacturer and put in the dispenser 14, the date and quantity of the order are erased and the quantity is added to the total quantity "to date". After a year, the "total quantity used" is observed and adjustment in the total number of suture packages 20 kept are made. Many variations of this exemplary inventory system are possible, to fit specific inventory and stock control needs.

The use of a transparent writing panel 30 is provided so that every package 20 of suture with its catalog number, size, length, needle and expiration date is visible. This use of a transparent writing panel 30 eliminates weekly counting of suture stock. By observing any type of suture, one can readily determine how many packages 20 are missing from the predetermined stock. For example, if nine packages 20 of a certain type of suture are kept and only five are in an exemplary nine box sector 40, then four additional packages 20 should be ordered. The orientation structurally of shelves 24 and writing panel 30 allowing for the entry of packages at inlet 33 and the removal of packages of 20 from outlet 34, assures that the sutures are automatically rotated. The number of packages 20 kept for a given suture type in a sector between shelves 24, can be adjusted by simply changing a shelf 24 to increase or decrease the number of packages 20 kept in a given sector 40, and by attaching an appropriately sized writing panel 30 to provide inlet 33 and outlet 34. The use of a plurality of dispenser boxes 14 having adjustable sectors assures that an original order of sutures can be maintained. That is, new stock can be added to the inventory by the addition of a new dispenser box 14 to an existing series of boxes 14.

The combined suture dispensing and inventory control system of the present invention adapts easily to the "Exchange Cart System" of distributing hospital supplies. In an "Exchange Cart System", supplies are kept in a central supply area with several rolling storage carts provided to carry specific supplies to various specialty areas of the hospital. In such a system, each "cart" contains a "mini-inventory" of supplies suited to the needs of the respective area to which it is sent. During a given day, one cart is in use, at its area of need, and an identical replacement cart is being prepared at the central supply. With the present invention, each cart could be equipped with a dispensing box 14, having individual sectors 40 containing suture types to best fit the area to be served.

The present invention provides an enclosed housing for suture packages 20 which is relatively clean and free from dust. The entire suture stock is portable, being slideably mountable on a wall rack 12. Wall rack 12 is comprised of a pair of horizontally deposed brackets 13 having an outward lip 15. Each dispenser box 14 is provided with an extended lip 16' of back wall 16 which lip slideably fixed and is engaged and held by the lip 15 of bracket 13. FIG. 1 illustrates the use of brackets 13 to retain and hold a plurality of dispenser boxes 14.

Because many varying and differing embodiments may be made within the scope of the inventive concept herein taught, and because many modifications may be made in the embodiment herein detailed in accordance with the descriptive requirements of law, it is to be understood that the details herein are to be interpreted as illustrative and not in a limiting sense.

What is claimed as invention is:

1. A combined package dispensing and inventory control system for packages having descriptive information on their exterior, for example, surgical suture packages, comprising:

a. at least one, elongated dispensing box each forming means for holding the packages having descriptive information thereon at the front of said box, each said box being provided with top, bottom, back and side walls but having an open front portion, each of said boxes being further provided with a plurality of inner shelf supporters on its walls; said dispensing box having a cross-sectional dimension which will allow for the stacking vertically within the said dispensing box a plurality of, for example, conventional surgical suture packages, said packages having written information thereon;

b. a plurality of shelves horizontally mountable on at least some of the inner shelf supporters of said boxes;

c. at least one panel means removably attachable to the front portion of each of said boxes, said panel means providing a writing surface thereon, said panel means dimensioned and so attachable to said box between two of said shelves as to provide an inlet above said panel and below a first, upper one of said shelves for the addition of, for example, surgical suture packages, to said box and an outlet below said panel and above a second, lower one of said shelves for the removal of said packages from said box; and said panel means being transparent, the descriptive information on said packages being visible through said panel means; rack means attachable to a support structure, for example, a wall, for the storage of at least one of said elongated dispensing boxes, said elongated dispensing boxes laterally movable on said rack means.

2. The apparatus defined in claim 1, wherein said rack means is a pair of substantially horizontally attachable grooved supports, and each of said elongated boxes is provided with a projecting lip means on said box, said lip means engaging the groove portion of said rack to support said dispensing box in a substantially vertical position, said dispensing boxes abutting one another and being slidable in a substantially horizontal direction on said rack means.

3. A method for the storing and inventory control of, for example, surgical suture packages, comprising the steps of:

a. providing a surgical suture package dispensing system, which system comprises:

i. at least one, elongated dispensing box, provided with top, bottom, back and side walls, said box having an open front portion, said box provided with a plurality of inner groove slots; said dispensing box having a crosssectional dimension which will allow for the stacking vertically within the said dispensing box a plurality of, for example, conventional surgical suture packages, said packages having written information thereon;

ii. a plurality of shelves, horizontally mountable in the slot portion of said boxes; and iii. at least one transparent panel means attachable to the front portion of said boxes, said transparent panel means providing a writing surface thereon, said panel means dimensioned and so attachable to said box between the two of said shelves as to provide an inlet above said panel and below one of said shelves for the addition of, for example, surgical suture packages to said box, and an outlet below said panel for the removal of said packages from said box, the packages having descriptive information thereon which is visible through the transparent panel means;

b. adding packages of surgical suture to the elongated dispensing box in a vertical stack between two of the horizontally mounted shelves in the dispensing box, the addition of the surgical suture packages made through the inlet portion of the dispensing package 2, and the packages stacked vertically on a lower horizontally mounted shelf;

c. arranging like types of suture package in a separate sector of the suture dispensing box, each sector having an inlet portion for the addition of newer like packages of suture and each sector having an outlet portion for the removal of older like packages for suture; and d. writing inventory information on the panel means of the dispensing box.

* * * * *